(12) United States Patent
Humphrey

(10) Patent No.: US 9,974,498 B2
(45) Date of Patent: May 22, 2018

(54) RADIOGRAPHY IMAGING SYSTEM

(71) Applicant: Original Design Services Limited, Horsham, West Sussex (GB)

(72) Inventor: Malcolm Humphrey, Horsham (GB)

(73) Assignee: ORIGINAL DESIGN SERVICES LIMITED, Horsham, West Sussex (GB)

( * ) Notice: Subject to any disclaimer, the term of this patent is extended or adjusted under 35 U.S.C. 154(b) by 200 days.

(21) Appl. No.: 14/400,211

(22) PCT Filed: May 8, 2013

(86) PCT No.: PCT/GB2013/000199
§ 371 (c)(1),
(2) Date: Nov. 10, 2014

(87) PCT Pub. No.: WO2013/167855
PCT Pub. Date: Nov. 14, 2013

(65) Prior Publication Data
US 2015/0098549 A1   Apr. 9, 2015

(30) Foreign Application Priority Data

May 9, 2012   (GB) .................................. 1208062.8

(51) Int. Cl.
*A61B 6/00* (2006.01)
*G01T 1/20* (2006.01)
(Continued)

(52) U.S. Cl.
CPC .............. *A61B 6/4233* (2013.01); *A61B 6/42* (2013.01); *A61B 6/4208* (2013.01); *G01T 1/20* (2013.01);
(Continued)

(58) Field of Classification Search
CPC ....... A61B 6/42; A61B 6/4208; A61B 6/4233; G01T 1/20; G01T 1/2002; G01T 1/2006; G01T 1/2018
(Continued)

(56) References Cited

U.S. PATENT DOCUMENTS 4,737,641 A   4/1988   Lange et al.
4,936,678 A   6/1990   Gordon et al.
(Continued)

FOREIGN PATENT DOCUMENTS

BE   1008234 A5   2/1996
EP   0131154 A1   1/1985
(Continued)

OTHER PUBLICATIONS

Arda D. Yalcinkaya, Hakan Urey, and Sven Holmstrom, NiFe Plated Biaxial MEMS Scanner for 2-D Imaging, IEEE Photonics Technology Letters, vol. 19, No. 5, Mar. 1, 2007, pp. 330-332.*
(Continued)

*Primary Examiner* — Allen C. Ho
(74) *Attorney, Agent, or Firm* — David D. Brush; Westman Champlin & Koehler, P.A.

(57) ABSTRACT

Apparatus for radiography is disclosed, which includes a flat panel scintillator having a first surface for being exposed to radiation and a second surface for emitting visible light in response, and an associated imaging system. The imaging system includes a plurality of scanning MEM mirrors, each associated with a respective sub-region of the scintillator second surface, each scanning MEM mirror being mounted and controlled so as to re-direct light from along a predetermined scan path within the respective sub-region towards a respective optical channel. A photodetector is associated with each scanning MEM mirror and optical channel for receiving the re-directed light and generating an electrical
(Continued)

signal representing light intensity. A processor receives the electrical signal from each photodetector and the corresponding position of each scanning MEM mirror to generate therefrom a reconstructed two-dimensional image.

17 Claims, 7 Drawing Sheets

(51) Int. Cl.
G01T 1/24 (2006.01)
G02B 26/08 (2006.01)

(52) U.S. Cl.
CPC .......... *G01T 1/2002* (2013.01); *G01T 1/2006* (2013.01); *G01T 1/2014* (2013.01); *G01T 1/2018* (2013.01); *G02B 26/0833* (2013.01)

(58) Field of Classification Search
USPC ..................................... 378/98.8; 250/370.09
See application file for complete search history.

(56) References Cited

U.S. PATENT DOCUMENTS

| | | | | |
|---|---|---|---|---|
| 5,550,380 | A * | 8/1996 | Sugawara | A61B 6/145 250/368 |
| 5,734,476 | A | 3/1998 | Dlugos | |
| 6,115,114 | A | 9/2000 | Berg et al. | |
| 6,282,261 | B1 * | 8/2001 | Mazess | A61B 6/4225 348/E3.045 |
| 6,463,121 | B1 * | 10/2002 | Milnes | A61B 6/4482 378/62 |
| 6,656,528 | B2 * | 12/2003 | Ouellet | G02B 5/0891 204/192.26 |
| 6,710,350 | B2 * | 3/2004 | Ruzga | G01T 1/1642 250/366 |
| 6,987,835 | B2 * | 1/2006 | Lovoi | A61N 5/1001 378/119 |
| 7,129,601 | B2 * | 10/2006 | Brown | G02B 6/3572 310/12.31 |
| 7,136,547 | B2 * | 11/2006 | Brown | G02B 6/3572 359/198.1 |
| 7,522,701 | B2 * | 4/2009 | Jensen | A61B 6/481 378/162 |
| 7,910,891 | B2 * | 3/2011 | Cannon | G01T 1/20 250/368 |
| 7,929,664 | B2 * | 4/2011 | Goodenough | G01V 5/005 378/53 |
| 8,948,338 | B2 * | 2/2015 | Barbato | G01T 1/2018 250/370.09 |
| 2003/0168603 | A1 | 9/2003 | Ruzga | |
| 2010/0072378 | A1 | 3/2010 | Cannon | |
| 2015/0146854 | A1 | 5/2015 | Barbato et al. | |

FOREIGN PATENT DOCUMENTS

| | | |
|---|---|---|
| EP | 0314231 A2 | 5/1989 |
| EP | 2085117 A1 | 8/2009 |
| EP | 2773981 A1 | 9/2014 |
| WO | 2011107112 A1 | 9/2011 |
| WO | 2013066870 A1 | 5/2013 |

OTHER PUBLICATIONS

Great Britain Search Report dated Aug. 29, 2012 for corresponding Great Britain Patent Application No. 1208062.8, filed May 9, 2012.
International Search Report and Written Opinion dated Jan. 30, 2014 for corresponding International Patent Application No. PCT/GP2013/000199, filed May 8, 2013.
UKIPO Examination Report dated Mar. 30, 2016 for corresponding GB1208062.8, filed May 9, 2012.
Weston Aenchbacher et al., "Single-Pixel, MEMS Scanning Mirrir Camera", Photonics Conference (PH0), 2011 IEEE, IEEE, Oct. 9, 2011 (Oct. 9, 2011), pp. 849-850, XP032077693.
Everhart, "What is a Scintillator and how does it work", http://www.flatpaneldr.com/?p=443., WaybackMachine Jan. 12, 2011.

* cited by examiner

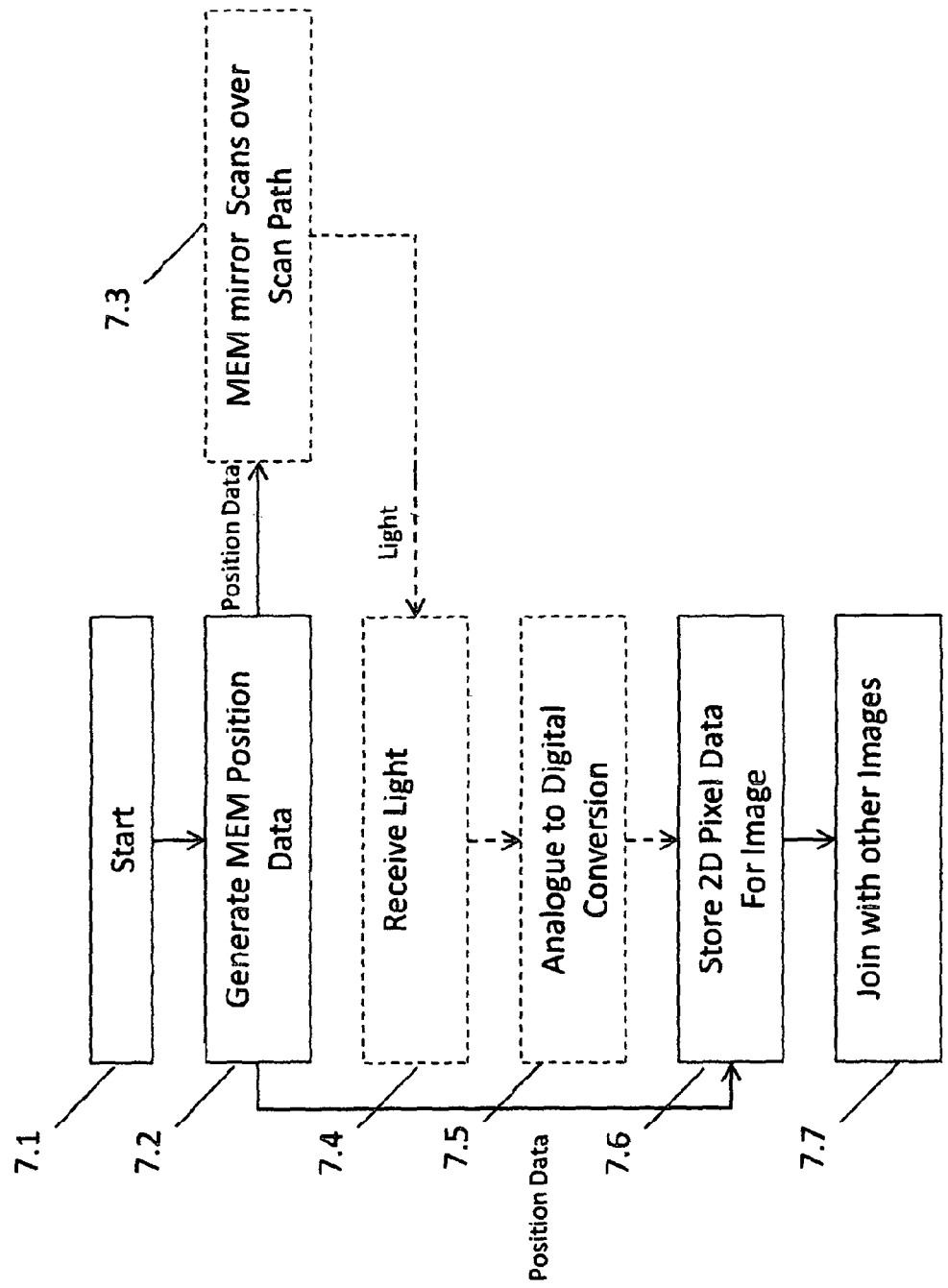

RADIOGRAPHY IMAGING SYSTEM

CROSS-REFERENCE TO RELATED APPLICATIONS

This Application is a Section 371 National Stage Application of International Application No. PCT/GB2013/000199, filed May 8, 2013, published as WO 2013/167855 A2 on Nov. 14, 2013, in English, which is based on and claims the benefit of United Kingdom Patent Application No. 1208062.8, filed May 9, 2012; the contents of which are hereby incorporated by reference in their entireties.

FIELD OF THE INVENTION

This invention relates to an apparatus and method for radiographic imaging.

BACKGROUND OF THE INVENTION

Radiography is the process of creating images by means of using radiation other than visible light. Perhaps the most well-known example is that of X-rays whereby ionising radiation is passed over an object to produce an image on a radiosensitive surface which can be used e.g. in healthcare, industry and testing, airport security systems and so on.

FIG. 1 shows a conventional digital X-ray system 1. It comprises a radiation source of X-ray photons 3, a scintillator 5, an amorphous silicon panel (ASP) 7, and read-out electronics 9. The scintillator 5 is formed of a material that emits visible light in response to X-ray absorption; it is usually in the form of a flat panel. The light is detected using the ASP 7 which is a relatively complex, expensive and bulky array of photodiodes or thin-film transistors (TFTs) that convert the light into electrical signals which are then interpreted and converted into data by the read-out electronics 9 to represent a two-dimensional image form.

Such a conventional digital X-ray system 1 has a high cost, which is dependent on size, not least because of the expense of the ASP 7 required. In addition, the useful life of such a conventional digital X-ray system 1 is limited because the light sensing elements (photodiodes or TFTs) of the ASP 7 are in practise exposed to radiation which damages the semiconductor material. Such a conventional digital X-ray system 1 is also susceptible to 'ghosting' which occurs when X-ray photons causes electrical charge effectively to be trapped in the semiconductor material resulting in previous images (or parts thereof) to appear in new and/or subsequent images. The spatial resolution offered by such a conventional digital X-ray system 1 is also limited by the pixel count, which results from the number of photodiodes and/or TFTS in the ASP 7 which cannot be varied once manufactured.

Additionally, such systems tend to have limited image readout speeds, meaning that the object or patient being imaged would have to be subjected to radiation for longer periods of time, increasing the dose received.

SUMMARY OF THE INVENTION

A first aspect of the invention provides apparatus for radiography, comprising: a scintillator having a first surface for being exposed to radiation and a second surface for emitting visible light in response; and an imaging system comprising: an optical channel; a scanning mirror for scanning a two-dimensional region of the scintillator second surface along a predetermined scan path so as to direct light emitted from the scanned region to the optical channel; means for detecting the light received from the optical channel; and means for generating, using said received light and the corresponding scan path position, a signal or data for representing a two-dimensional image indicative of the light emitted from the two dimensional region of the scintillator.

Such an apparatus provides improvements over conventional digital radiography apparatus. By imaging a two-dimensional surface of the scintillator using a scanning mirror and effectively transmitting the resulting light in serial-fashion for the different scan path positions, the photodetection stage(s) can use much simpler and less expensive technology.

Further, the overall apparatus can be made less bulky.

Further, the photodetection stage does not have to be adjacent nor in-line with the scintillator and can therefore be shielded from the radiation source to avoid adverse effects which may affect its operation.

The imaging system may further comprise an optical lens positioned between the scintillator and the scanning mirror for focussing light from the region of said second surface onto the scanning mirror.

The scanning mirror of the imaging system may be a micro electromechanical (MEM) mirror.

The scanning mirror of the imaging system may have an associated position control system configured to cause multi-axis movement of said mirror in accordance with the predetermined scan path.

The optical channel of the or each imaging system may be an optical fibre having an input end and an output end.

The apparatus may further comprise an optical lens positioned between the scanning mirror and the input end of the optical fibre for focussing light directed from the mirror into said input end.

The light detecting means may comprise a photodetector, e.g. a photodiode, for generating an electrical signal representing received light intensity. The light detecting means may be a single photodetector.

The image generating means may comprise an analogue to digital converter (ADC) for converting the electrical signal generated by the photodetector into light intensity data and processing means for correlating the light intensity data to its corresponding scan path position.

The apparatus may further comprise a display for outputting the two-dimensional reconstructed image.

The apparatus may further comprise a radiation source for directing radiation towards the scintillator first surface and wherein the light detecting means is shielded from the radiation source.

In the preferred embodiment, a plurality of the above-described imaging systems are provided, each system being associated with a respective sub-region of the scintillator second surface.

As a result of the parallel nature of the image capture, overall image capture speeds can be increased over conventional ASP's resulting in a reduction in dose to the patient or object being imaged.

The apparatus may further comprise means for operating a subset of the imaging systems so as to scan its or their two-dimensional region at a greater resolution than those of the other imaging system(s). Said operating means may be configured to cause the scanning mirror of the or each subset to scan a smaller two-dimensional region than those of the other imaging system(s). Said operating means may be configured to cause the image generating means of the or each subset to sample the electrical signal generated by the photodetector into light intensity data at a higher rate than those of the other imaging system(s). The operating means may include a user interface to enable user selection of said one or more subsets to scan at a greater resolution.

The apparatus may further comprise means for receiving each signal or data set representing the reconstructed two-dimensional image for a sub-region and generating a joined two-dimensional image indicative of the light emitted from the overall second surface.

A second aspect of the invention provides apparatus for use in radiography, comprising: a scintillator having a first surface for being exposed to radiation and a second surface for emitting visible light in response; and an imaging system comprising: a plurality of scanning mirrors, each associated with a respective sub-region of the scintillator second surface, each scanning mirror being mounted and controlled so as to re-direct light from along a predetermined scan path within the respective sub-region towards a respective optical channel; photodetection means associated with each scanning mirror and optical channel for receiving the re-directing light and generating an electrical signal representing light intensity; and processing means for receiving the electrical signal from each photodetection means and the corresponding position of each mirror to generate therefrom a reconstructed two-dimensional image indicative of the light emitted from each scintillator sub-region.

A third aspect of the invention provides a method for performing radiography, comprising: operating a scanning mirror to scan a two-dimensional region of a scintillator light-emitting surface along a predetermined scan path so as to direct light emitted from the scanned region to a light-carrying optical channel; detecting the light received from the scanning mirror by means of the optical channel; and generating, using said received light and the corresponding scan path position from which the light was received, a signal or data for representing a two-dimensional image indicative of the light emitted from the two dimensional region of the scintillator.

A fourth aspect of the invention provides a computer program comprising instructions that when executed by a computer apparatus control it to perform the method defined in the third aspect.

A fifth aspect of the invention provides a non-transitory computer-readable storage medium having stored thereon computer-readable code, which, when executed by computing apparatus, causes the computing apparatus to perform a method comprising: operating a scanning mirror to scan a two-dimensional region of a scintillator light-emitting surface along a predetermined scan path so as to direct light emitted from the scanned region to an optical channel; detecting the light received from the scanning mirror; and generating, using said received light and the corresponding scan path position, a signal or data for representing a two-dimensional image indicative of the light emitted from the two dimensional region of the scintillator.

BRIEF DESCRIPTION OF THE DRAWINGS

Embodiments will now be described, by way of non-limiting example only, with reference to the accompanying drawings, in which:

FIG. 7 is a flow diagram indicative of processing steps performed by the control module of the FIG. 2 system.

DETAILED DESCRIPTION OF A PREFERRED EMBODIMENT

Figure 2:
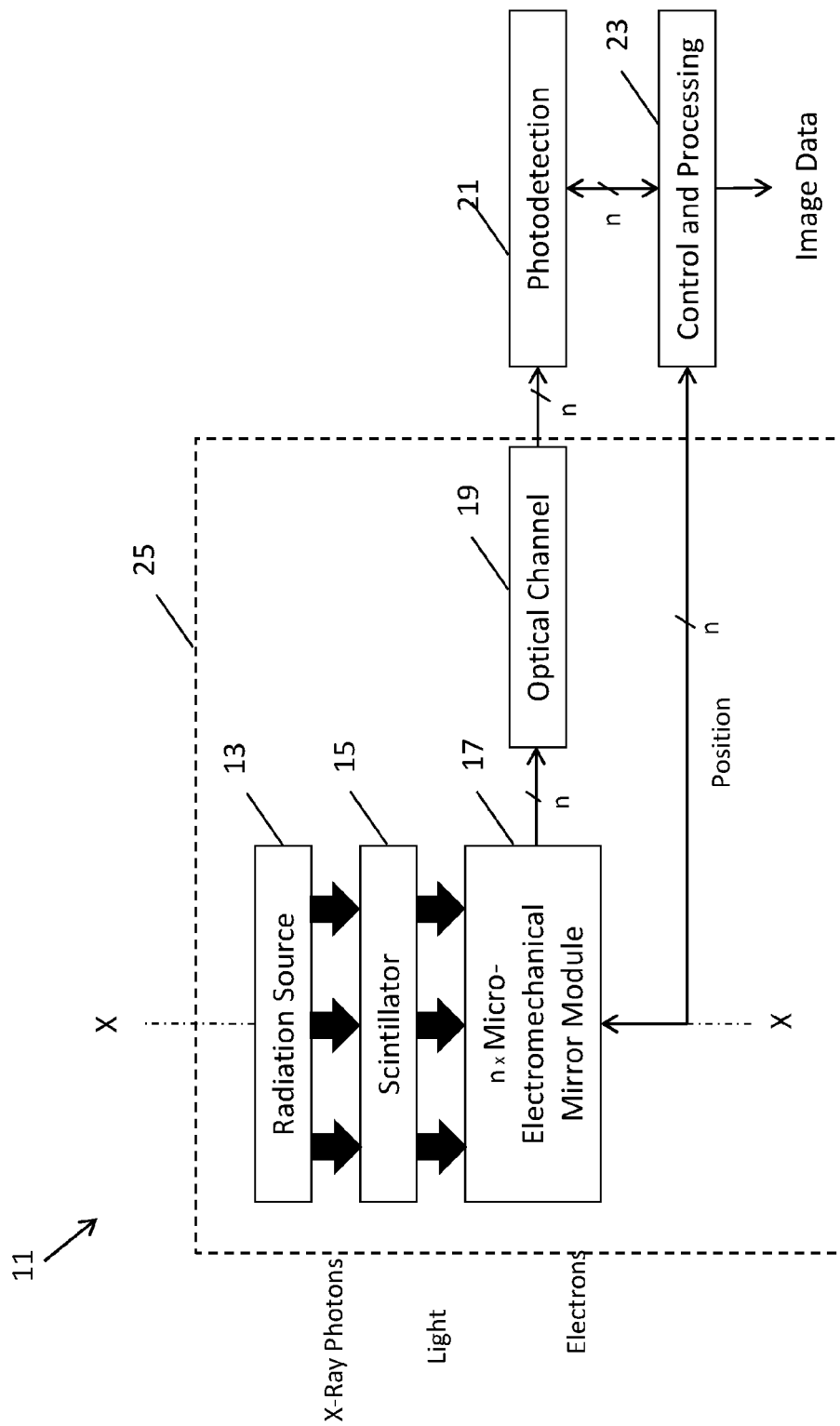
FIG. 2 is a schematic diagram of a digital X-ray system according to the invention.

Referring to FIG. 2, a digital X-ray system 11 in accordance with a first embodiment comprises a radiation source 13, a flat-panel scintillator 15, a Micro-Electromechanical (MEM) mirror module 17, an optical channel module 19, a photo detection module 21, and a control and processing module (hereafter "control module") 23.

The radiation source 13 is a conventional source of ionizing radiation for use in medical, industrial or security applications.

The flat-panel scintillator 15 is also conventional in terms of it having the same properties and form of commercially available flat-panel scintillators configured for medical, industrial or security applications. The flat-panel scintillator 15 in this case has a first, upper side which is exposed to radiation and an opposed, lower side which emits visible light in response to absorption of the radiation. Further details of scintillator technology can be found at http://www.flatpaneldr.com/?p=443 to give one example. It is assumed in this case that the scintillator upper and lower sides have a substantially rectangular, planar form.

In use, a subject such as person or article is positioned between the radiation source 13 and the flat-panel scintillator 15; the radiation absorbed by the flat-panel scintillator after it has passed around/through the subject is interpreted by the subsequent stages in order to generate the X-ray image.

The MEM mirror module 17 comprises an array of multiple (n) MEM mirrors. As will be known, a MEM mirror is a silicon (or integrated circuit (IC)) device having on one surface a small mirror connected typically to small flexures allowing it to move about multiple axes in response to control signals which cause the flexures to move. MEM mirrors currently find useful application in scanning systems, for example in image capture and image display technologies whereby a two-dimensional image can be reproduced or displayed pixel-by-pixel by means of the mirror scanning along a predetermined scan path.

Figure 1:
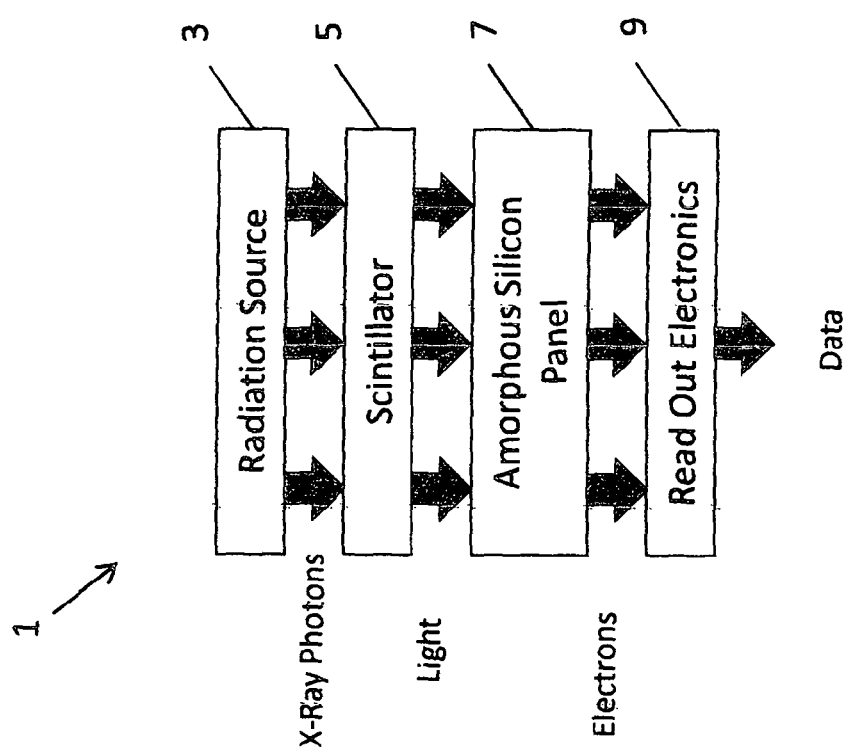
FIG. 1 is a schematic diagram of a conventional digital X-ray system.
Figure 3:
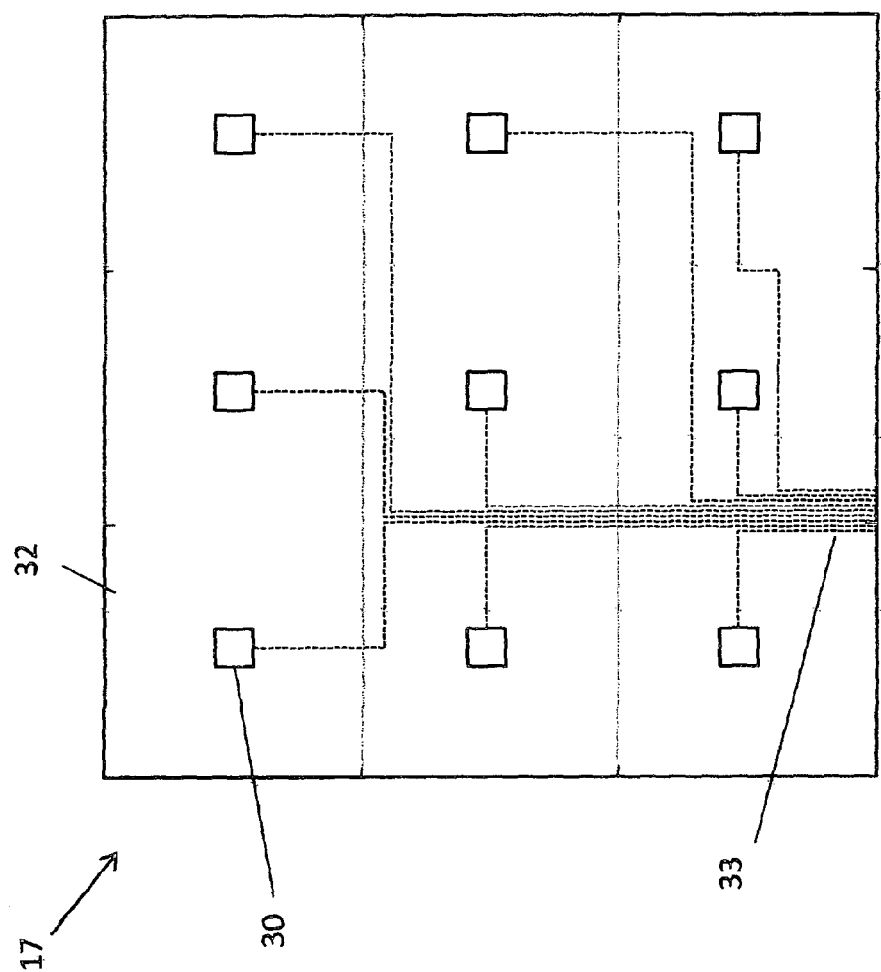
FIG. 3 is a plan view of a printed circuit board (PCB) on which is mounted micro electro-mechanical (MEM) mirrors used in the system of FIG. 2.

Referring to FIG. 3, the MEM mirror module 17 comprises an array of nine MEM mirror ICs (MEMs) 30 provided on a printed circuit board (PCB) 32, the MEMs being arranged in a 3×3 configuration as shown. Instead of a PCB, a mechanical plate can be used which tends to be less expensive. The PCB 32 has approximately the same rectangular shape as the flat-panel scintillator 15, although this is not essential, and is arranged below its lower surface in a vertical stack-like fashion. The mirror of each MEM mirror 30 is configured to move about a vertical and horizontal axis in accordance with control signals received from the control and processing module 23 to scan a predefined two-dimensional planar portion of the flat-panel scintillator 15. The control signals are transmitted to each MEM mirror 30 through respective wires 33 of an MEM bus, indicated by the dotted lines in FIG. 3. The mirror of each MEM mirror 30 is arranged at an obtuse angle to the flat-panel scintillator surface so as to direct light generally sideways from the scan path towards the capturing part of the digital X-ray system 11 to be described below. In the example shown in FIG. 2, the angle of redirection is substantially normal to the 'stacking axis' X-X. This helps reduce the dimensions of the digital X-ray system 11 because the image capturing parts of the digital X-ray system 11, particularly the photodetection module 21 and control module 23, are not stacked in alignment with the stacking axis X-X as is the case in conventional systems, for which see FIG. 1.

Figure 4:
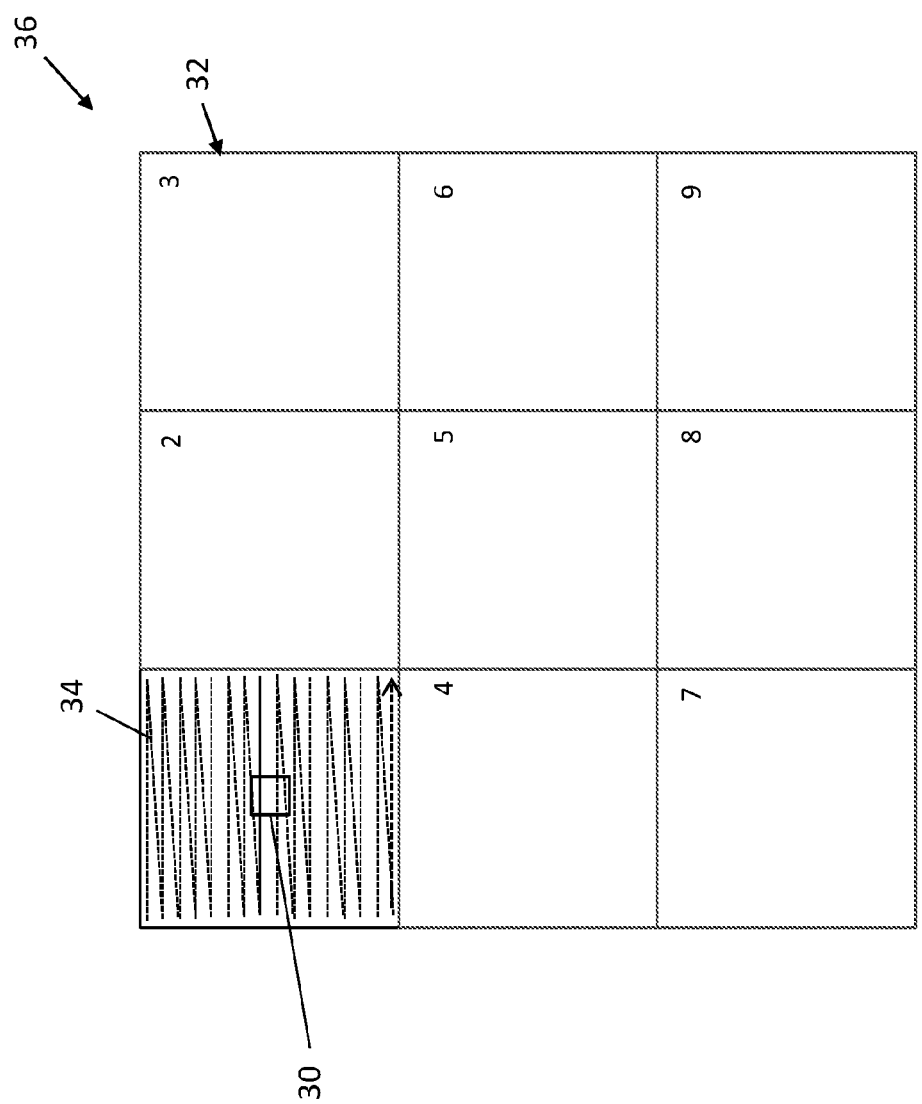
FIG. 4 is a plan view of the PCB of FIG. 3 overlaid with a surface of a scintillator used in the system of FIG. 2.

The scan path can follow any two-dimensional path and in this case follows a raster scan path. As shown in FIG. 4, which shows schematically the PCB 32 overlaid on the flat-panel scintillator 15 lower surface (with one MEM mirror 30 shown for ease of explanation) each MEM mirror 30 is arranged so as to scan a respective one of nine two-dimensional portions or 'footprints' 36 of the flat-panel scintillator's light-emitting surface. The raster scan path is indicated by dotted line 34. It will be appreciated that raster scan paths 34 can overlap on the periphery of each footprint 36 with image post-processing being used to handle recognition and removal of the overlapping content.

Referring back to FIG. 2, the optical channel 19 is arranged to receive the light reflected by each MEM mirror 30 and carry said light to the capturing part of the digital X-ray system 11, specifically to the photodetection module 21. The optical channel 19 here comprises n(=9) optical fibres, so that each MEM mirror 30 is paired with a corresponding optical fibre. A receiving end of each optical fibre is positioned so as to receive the light from the MEM mirror 30 with which it is paired and through total internal reflection carries it to an emitting end of said optical fibre at which point it is passed to the photodetection module 21.

The above-described radiation source 13, flat-panel scintillator 15, and MEM mirror module 17 are arranged within a shielded casing 25 or similar container which shields, absorbs and/or limits the amount of ionising radiation leaving the shielded casing 25 or containment which may otherwise cause the abovementioned adverse effects outlined in the background. The optical channel 19 can be within the shielded casing 25, completely or partially, and carries light to the external location where the photodetection module 21 and control and processing module 23 are located. By using flexible optical fibres, the light signals can be carried in any direction relative to the other parts of the digital X-ray system 11 which is convenient in terms of size.

The light carried by each optical fibre represents the light emitted from part of the scan path of a particular region. As the MEM mirror 30 scans along the scan path, the light intensity will vary and hence the optical fibre carries a serial representation of what is a two-dimensional image at a given point in time. This means that fewer photodetectors are required to convert the light signal to an electrical signal representing the two-dimensional image.

The photodetection module 21 comprises n photodiodes, one photodiode being associated with each optical fibre of the optical channel 19. Each photodiode is configured to generate an electrical signal representing the light received via the MEM mirror 30 and optical fibre from a respective region of the flat-panel scintillator 15. Each photodiode is connected to an analogue-to-digital converter (ADC) for generating data indicative of the light intensity for the region.

It will be appreciated that a small number of relatively inexpensive photodiodes is therefore utilised instead of the bulky and expensive ASP module referred to in the background.

The control and processing module 23 is configured to perform the following functions:

(1) to generate control signals for each of the nine MEM mirrors 30 to control their vertical and horizontal position to move in accordance with the raster scan path 34. The control module 23 includes a memory storing data representing said raster scan path 34. The control module 23 therefore knows the scan path position at a given instant in a scan cycle for each MEM mirror 30;

(2) to construct a two-dimensional image for each of the n scintillator regions using the received light intensity data and corresponding position data; and (3) to construct a two-dimensional image representing the joining of the images constructed in (2) above, to represent the overall scintillator output.

The above functions can be performed in real time in the case of a moving subject, e.g. an item of luggage passing through a security scanner.

Preferably, an optical lens is provided between each scintillator region and its corresponding MEM mirror 30 in order to focus emitted light onto the MEM mirror 30.

A further optical lens can also be provided between the MEM mirror 30 and the input end of its corresponding optical fibre, again for focussing light reflected from the MEM mirror 30 into said input end.

Figure 5:
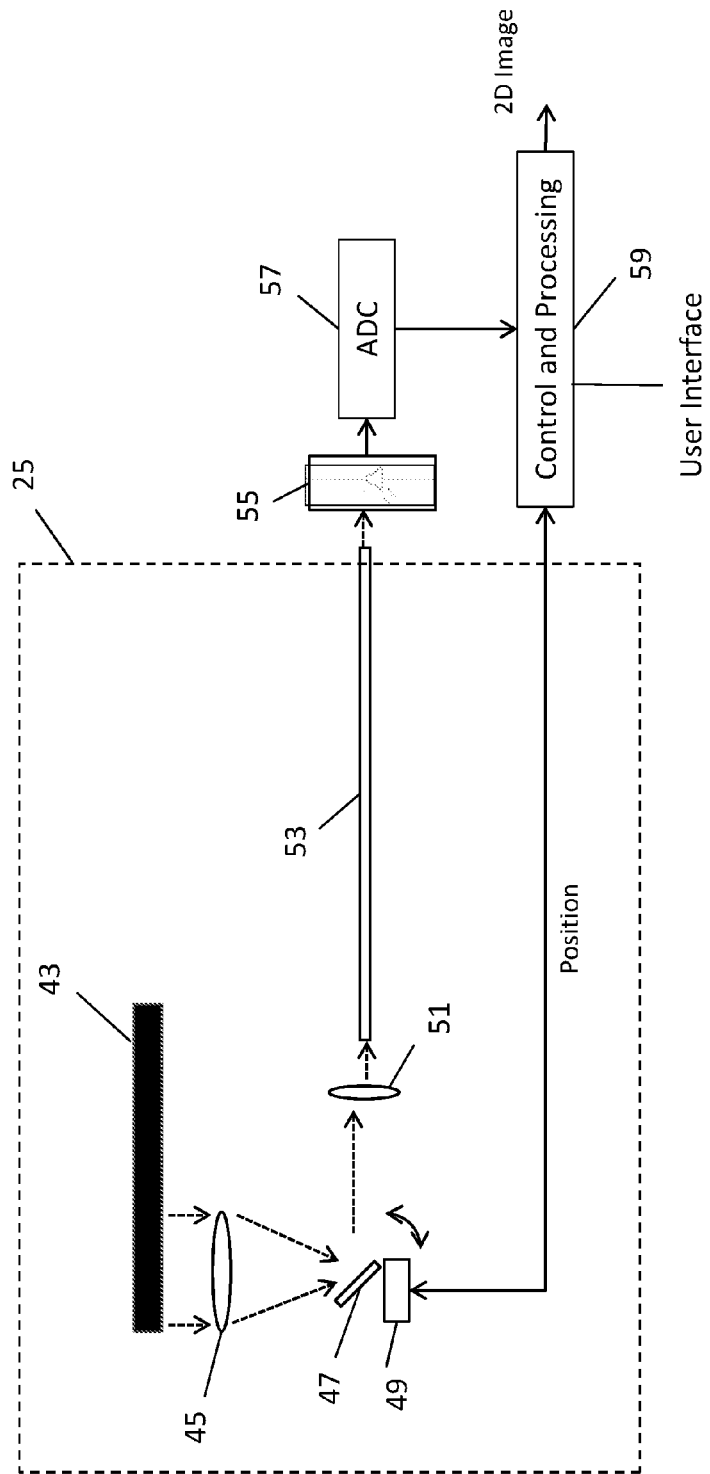
FIG. 5 is a schematic diagram of one part of the digital X-ray system of FIG. 2 which is useful for understanding its operation.

Referring now to FIG. 5, for completeness, an explanation of the digital X-ray system 11 will now described in terms of its operation with respect to just one flat-panel scintillator region, namely Region 1 shown in FIG. 4.

The flat-panel scintillator is again indicated by reference numeral 43. A lens 45 is disposed underneath Region 1 of the flat-panel scintillator 43, between it and its MEM device 49 having an MEM mirror 47 axially aligned beneath the lens 45. The lens 45 focuses the light received from Region 1 onto the MEM mirror 47 which scans over the focussed image and directs it sideways, generally normal to the scan axis, towards a corresponding optical fibre 53. A further lens 51 is disposed between the MEM mirror 47 and the input end of the optical fibre 53.

The optical fibre 53 carries the varying light signal to a position external to the shielded casing 25. At this external position, a single photodiode 55 receives the light and converts it into an electrical signal representing the varying light intensity along the raster scan path 34 of Region 1. The electrical signal is converted to data by an ADC 57. The data for Region 1 is then outputted to the control and processing module 59.

The control and processing module 59 is responsible for generating control signals for input to the MEM mirror device 49 which moves the MEM mirror 47 by means of its flexures. Therefore, the control and processing module 59 is also configured to identify from which part of the raster scan path (and therefore the two dimensional part of Region 1) the received signal corresponds. Data corresponding to the light intensity at each of a plurality of scan positions is therefore generated and stored as pixel data on memory of the control and processing module 59 for processing and display.

The control and processing module 59 therefore generates in real-time (or near real-time) an image representing Region 1 of the flat-panel scintillator 43. The same process is performed in parallel for each of Regions 2-9 shown in FIG. 4 and the control and processing module 59 generates a joined image representing all regions in the 3×3 configuration shown in FIG. 4.

Figure 6:
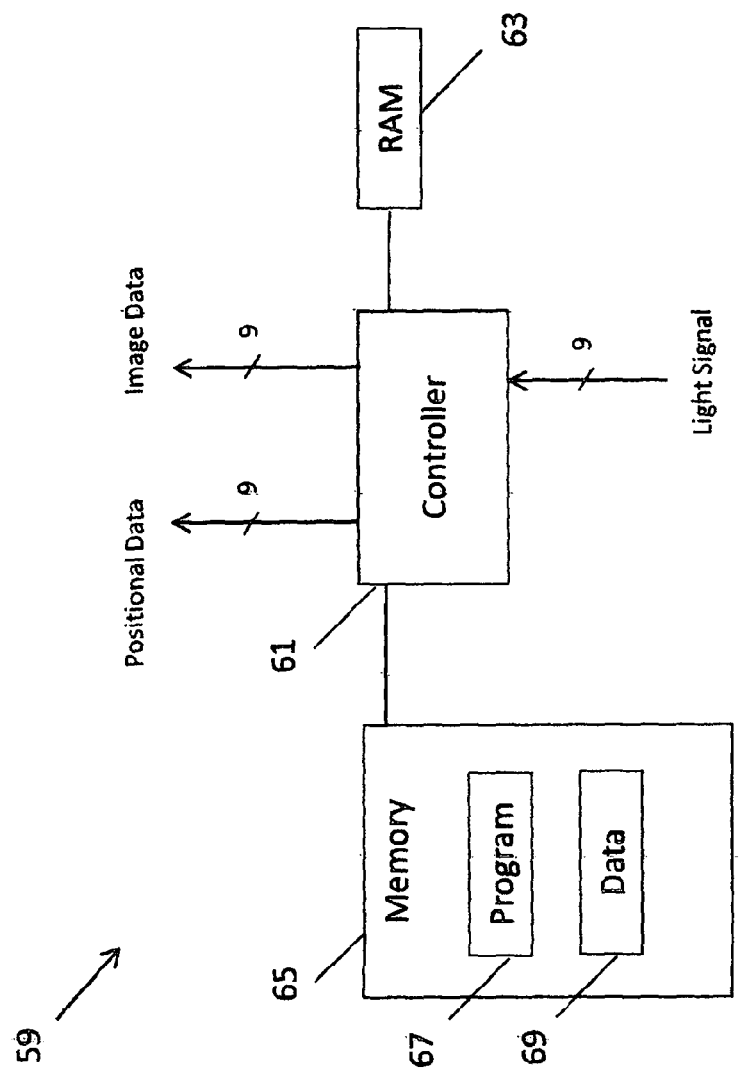
FIG. 6 is a schematic diagram of a control module of the FIG. 2 system.

The control and processing module 59 may comprise a dedicated processing module, e.g. a microcontroller or FPGA configured to operate under the control of a program. FIG. 6 shows functional components, including a controller 61, RAM 63, a memory 65 an input bus for the light data, and output buses for the positional data and image data. The controller 61 is connected to each of the other devices to control operation thereof. RAM 63 is used by the controller 61 for the temporary storage of data. The memory 65 stores one or more programs 67 having code which, when executed by the controller 61 in conjunction with RAM 63, controls the overall digital x-ray system 11. The memory 65 also stores data 69 representing pixels of the two dimensional scan images for output to a display system, such as a computer monitor.

Referring to FIG. 7, the main steps performed by the program 67 will now be described in relation to one of the scan regions, e.g. Region 1. Those steps shown in dotted line are not part of the program 67 itself but are useful for understanding the process.

The process starts at step 7.1 which is at the start of a scan cycle. In step 7.2, the MEM position data is generated for each step of a scan cycle. In step 7.3, the position data for the current step is received by the MEM device 49 and the MEM mirror scans to the appropriate position. In step 7.4, light is received from the scanning MEM mirror 47 and is carried to the photodiode 55. In step 7.5, the signal from the photodiode 55 is analogue-to-digital converted by an ADC 57. In step 7.6, a correlation is made between the received light intensity data and the positional data for the current step of the scan cycle so that each pixel of the 2D Region is generated and stored. In step 7.7 the resulting image is joined with images generated in the above manner for the other Regions.

Spatial resolution for a given scan region is governed by its 2D scan area and/or the sampling speed of the ADC 57. By reducing the scan area, for example, the spatial resolution is improved allowing smaller features to be imaged. This is in effect an optical zoom feature. The scan area may also be offset to allow the zooming to be targeted to within a particular area within the MEM's field of view. This gives the option of generating a composite image where, say, one mirror is operated to scan at a higher resolution over a relatively small area with the other mirrors scanning at, relatively speaking, a lower resolution with a wider field of view to provide 100% coverage. The overall image produced can therefore show an area-of-interest in higher detail than the rest of the image, enabling for example an area of the body to be imaged in greater detail than the rest. A user interface associated with the control and processing module 59 may be configured to allow selection of a subset (one or more) of the regions for higher resolution scanning by causing the MEM mirror 47 and/or ADC 57 of said region(s) to operate accordingly. The extent to which the scan area of the selected region(s) is or are reduced can be user defined through the interface. The remaining region(s)' wider field-of-view may be determined automatically to obtain full coverage of the overall imaging area.

In the above embodiment, the use of electromagnetically actuated MEM mirrors with associated lens and optical fibre parts means the active, contained, area 25 of the overall digital x-ray system 11 is effectively radiation hardened, making it useful for high energy radiation imaging such as that used on radiotherapy equipment where it is desirable to use treatment radiation for portal imaging. Also, because the photodetector module 21 is outside the radiation field, such a system should not suffer from the ghosting found in conventional imaging devices which will improve image quality.

As a result of the parallel nature of the image capture, overall image capture speeds can be increased over conventional ASP's resulting in a reduction in dose to the patient or object being imaged.

It will be appreciated that the above described embodiments are purely illustrative and are not limiting on the scope of the invention. Other variations and modifications will be apparent to persons skilled in the art upon reading the present application.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. An apparatus for radiography, comprising:
   a scintillator having a first surface for being exposed to radiation and a second surface for emitting visible light in response;
   at least one imaging system, each of the at least one imaging system comprising:
   an optical channel;
   a scanning mirror under the second surface of the scintillator arranged to scan a two-dimensional region of the second surface of the scintillator by multi-axis movement along a predetermined two-dimensional scan path so as to re-direct the visible light emitted from the scanned two-dimensional region to the optical channel;
   a photodetector separate from the scanning mirror arranged to detect the visible light re-directed by the scanning mirror and received from the optical channel; and
   means for generating, using said received visible light and a corresponding position on the two-dimensional scan path, a signal or data representing a two-dimensional image indicative of the visible light emitted from the two-dimensional region of the second surface;
   a radiation source for directing radiation towards the first surface of the scintillator, and wherein the photodetector is shielded from the radiation source; and
   a radiation blocking or absorbing shield configured to surround the radiation source, the scintillator, and the scanning mirror.

2. The apparatus according to claim 1, wherein each of the at least one imaging system further comprises an optical lens positioned between the scintillator and the scanning mirror for focussing visible light from the two-dimensional region of said second surface onto the scanning mirror.

3. The apparatus according to claim 1, wherein the scanning mirror comprises a micro-electromechanical (MEM) mirror.

4. The apparatus according to claim 1, further comprising an associated position control system configured to cause the multi-axis movement of the scanning mirror in accordance with the predetermined two-dimensional scan path.

5. The apparatus according to claim 1, wherein the optical channel further comprises an optical fibre having an input end and an output end.

6. The apparatus according to claim 5, further comprising an optical lens positioned between the scanning mirror and the input end of the optical fibre for focussing visible light directed from the scanning mirror into said input end.

7. The apparatus according to claim 1, wherein the photodetector comprises a photodiode, which generates an electrical signal representing received light intensity.

8. The apparatus according to claim 7, wherein the means for generating a signal or data comprises an analog-to-digital converter for converting the electrical signal generated by the photodetector into light intensity data and processing means for correlating the light intensity data to its corresponding position on the two-dimensional scan path.

9. The apparatus according to claim 1, further comprising a display for outputting the two-dimensional image.

10. The apparatus according to claim 1, wherein the at least one imaging system comprises a plurality of imaging systems, each of the plurality of imaging systems being associated with a respective sub-region of the second surface of the scintillator.

11. The apparatus according to claim 10, further comprising means for receiving each signal or data representing the two-dimensional image for a sub-region and generating a joined two-dimensional image indicative of the visible light emitted from the overall second surface.

12. The apparatus according to claim 10, wherein a subset of the plurality of imaging systems is configured to cause the scanning mirror of each imaging system of the subset to scan a smaller two-dimensional region than those of the other imaging system(s) of the plurality of imaging systems.

13. The apparatus according to claim 10, wherein a subset of the plurality of imaging systems is configured to cause the means for generating a signal or data representing a two-dimensional image of each imaging system of the subset to sample the electrical signal generated by the photodetector into light intensity data at a higher rate than those of the other imaging system(s) of the plurality of imaging systems.

14. The apparatus according to claim 10, further comprising a user interface to enable user selection of one or more subsets of the plurality of imaging systems to scan at a greater resolution.

15. The apparatus according to claim 1, wherein the photodetector is not under the second surface of the scintillator, and the scanning mirror is arranged to redirect visible light in a direction that is substantially parallel to the second surface of the scintillator, towards the optical channel.

16. An apparatus for use in radiography, comprising:
a scintillator having a first surface for being exposed to radiation and a second surface for emitting visible light in response;
an imaging system comprising:
a plurality of optical channels;
a plurality of scanning mirrors, positioned under the second surface of the scintillator, each of the plurality of scanning mirrors being associated with a respective sub-region of the second surface of the scintillator, each of the plurality of scanning mirrors being mounted and controlled for multi-axis movement so as to re-direct visible light from along a predetermined two-dimensional scan path of the second surface of the scintillator within the respective sub-region towards a respective one of the plurality of optical channels;
at least one photodetector which is separate from, and associated with each scanning mirror and each optical channel for receiving the re-directed visible light from the plurality of scanning mirrors and generating an electrical signal representing visible light intensity; and
a processor, which is configured to receive the electrical signal from the at least one photodetector and a corresponding position of each scanning mirror and generate therefrom a reconstructed two-dimensional image indicative of the visible light emitted from each sub-region;
a radiation source for directing radiation towards the first surface of the scintillator, and wherein the at least one photodetector is shielded from the radiation source; and
a radiation blocking or absorbing shield configured to surround the radiation source, the scintillator, and the plurality of scanning mirrors.

17. An apparatus for radiography, comprising:
a scintillator having a first surface for being exposed to radiation and a second surface for emitting visible light in response;
a plurality of imaging systems, each of the plurality of imaging systems being associated with a respective two-dimensional sub-region of the second surface of the scintillator and comprising:
an optical channel;
a scanning mirror under the second surface of the scintillator arranged to scan the respective two-dimensional sub-region of the second surface of the scintillator along a predetermined two-dimensional scan path so as to re-direct the visible light emitted from the scanned two-dimensional sub-region to the optical channel;
a photodetector separate from the scanning mirror arranged to detect the visible light re-directed by the scanning mirror and received from the optical channel; and
a processor, which is configured to receive an electrical signal from the photodetector and a corresponding position of the scanning mirror, and generate therefrom a reconstructed two-dimensional image indicative of the visible light emitted from the respective two-dimensional sub-region of the second surface of the scintillator, wherein a subset of the plurality of image systems is configured to scan the respective two-dimensional sub-region at a greater resolution than those of the other of the plurality of imaging systems.

* * * * *